United States Patent [19]
Crawford et al.

[11] Patent Number: 5,287,276
[45] Date of Patent: Feb. 15, 1994

[54] LOCALIZED MOTION ARTIFACT REDUCTION IN PROJECTION IMAGING

[75] Inventors: Carl R. Crawford, Milwaukee, Wis.; Cameron J. Ritchie, Seattle, Wash.

[73] Assignee: General Electric Company, Milwaukee, Wis.

[21] Appl. No.: 964,335

[22] Filed: Oct. 22, 1992

Related U.S. Application Data

[63] Continuation-in-part of Ser. No. 615,778, Nov. 19, 1990, Pat. No. 5,251,128.

[51] Int. Cl.$^5$ .............................................. G06F 15/42
[52] U.S. Cl. ............................ 364/413.19; 364/413.14
[58] Field of Search ...................... 364/413.13, 413.14, 364/413.15, 413.16, 413.17, 413.19; 128/653.2

[56] References Cited

U.S. PATENT DOCUMENTS

| | | | |
|---|---|---|---|
| 4,144,569 | 3/1979 | Wagner | 364/413.16 |
| 4,272,820 | 6/1981 | Lux | 364/413.19 |
| 4,387,722 | 6/1983 | Kearns | 128/716 |
| 4,564,017 | 1/1986 | Glover | 128/653.2 |
| 4,567,893 | 2/1986 | Charles et al. | 128/653.2 |
| 4,570,224 | 2/1986 | Shimoni et al. | 364/413.16 |
| 4,614,195 | 9/1986 | Bottomley et al. | 128/653.2 |
| 4,663,591 | 5/1987 | Pelc et al. | 324/309 |
| 4,682,109 | 7/1987 | Cuppen | 324/309 |
| 4,703,424 | 10/1987 | Gullberg et al. | 364/413.21 |
| 4,712,560 | 12/1987 | Schaefer et al. | 128/653.2 |
| 4,728,890 | 3/1988 | Pattany et al. | 324/309 |
| 4,730,620 | 3/1988 | Bailes | 128/653.2 |
| 4,779,620 | 10/1988 | Zimmermann et al. | 128/653.2 |
| 4,812,983 | 3/1989 | Gullberg et al. | 364/413.17 |
| 4,855,910 | 8/1989 | Bohning | 364/413.13 |
| 4,926,124 | 5/1990 | Le Roux | 324/309 |
| 4,937,526 | 6/1990 | Ehman et al. | 324/309 |
| 4,994,965 | 2/1991 | Crawford et al. | 364/413.15 |
| 5,032,990 | 7/1991 | Eberhard et al. | 364/413.15 |
| 5,035,244 | 7/1991 | Stokar | 128/653.2 |
| 5,056,020 | 10/1991 | Feldman et al. | 364/413.19 |

OTHER PUBLICATIONS

*IEEE Engineering in Med. & Bio. Society*, 11th Annual Conf., 1989, Catalog No. CH2770-6/89/000-0485, Crawford et al., "Reduction of Motion Artifacts in Computed Tomography".

*IEEE Transactions on Med. Imaging*, vol. 9, No. 3, Sep. 1990, Mitsa et al., "Correction of Periodic Motion Artifacts Along the Slice Selection Axis in MRI", pp. 310–317.

*IEEE Transactions on Medical Imaging*, vol. 10, No. 1, Mar. 1991, Atalar, "A Respiratory Motion Artifact Reduction Method in Magnetic Resonance Imaging of the Chest", pp. 11–24.

Reconstruction Algorithm for Fan Beam with a Displaced Center-of Rotation by Grant T. Gullberg et al., IEEE Transactions on Medical Imaging, vol. MI-5, No. 1 Mar. 1986.

Reconstruction for fan beam with an angular-dependent displaced center-of-rotation, Carl R. Crawford et al., Med. Phys. 15(1), Jan./Feb. 1988.

*Primary Examiner*—Roy N. Envall, Jr.
*Assistant Examiner*—David Huntley
*Attorney, Agent, or Firm*—Quarles & Brady

[57] ABSTRACT

An x-ray CT scanner acquires projection data from a series of projections during a scan of a patient's chest Movement of the patient's chest due to respiration is also sensed during the scan and this acquired motion data is employed along with an warping function which models chest motion to calculate factors which correct the acquired projection data and reduce motion artifacts in an image produced by back projecting the acquired projection data.

9 Claims, 5 Drawing Sheets

LOCALIZED MOTION ARTIFACT REDUCTION IN PROJECTION IMAGING

This patent is a continuation-in-part of patent application Ser. No. 07/615,778, filed Nov. 19, 1990, now U.S. Pat. No. 5,251,128, and entitled: Moton Artifact Reduction in Projection Imaging.

BACKGROUND OF THE INVENTION

The present invention relates to medical imaging, and particularly, to the reduction of motion artifacts in images produced using a projection method of reconstruction.

There are a number of modalities used to produce medical images. These include x-ray computed tomography (CT), magnetic resonance imaging (MRI), single photon emission computed tomography (SPECT), and positron emission computed tomography (PET) methods. In all cases, the data used to reconstruct the desired image are acquired over a period of time in a scan comprised of a series of projections. Each projection is a snapshot of the patient from a different angle, or perspective, and a scan typically includes tens, or hundreds of projections. In the case of x-ray CT the entire data set may be acquired in a few seconds, whereas an MRI scan typically requires a few minutes to complete. The methods used to reconstruct an image from such data sets presume that the patient is motionless during the entire scan and that the same fixed object is the subject of all acquired projections. To the extent this is not true, artifacts such as ghosts, smearing and fuzziness appear in the reconstructed image.

Efforts to reduce patient motion during a scan can significantly improve image quality. However, artifacts caused by respiration are a significant problem in chest scans where suspension of breathing is not possible or poor instructions are provided to the patient by the scanner operator. Children and comatose patients are routinely scanned with no attempt to synchronize respiration with scanning, and it is expected in such cases that a number of poor quality images will be produced and will be discarded.

One approach to reducing motion artifacts in medical images is to retrospectively correct the acquired data to offset the effects of motion. One such method, for example, is disclosed in U.S. Pat. No. 4,937,526 and is applied to acquired MRI data. The corrections that are made may be determined from an examination of the acquired raw data itself, or additional information, such as a signal from a cardiac monitor or a respiration monitor, may be used. The manner in which the corrections are made to the acquired raw data is determined by the particular reconstruction technique that is used. In the above patent, for example, a 2D Fourier transformation is used to reconstruct an image from the acquired MRI data, and the correction methods disclosed are limited to that technique.

The back projection method for image reconstruction is employed to some extent in all computed medical imaging modalities. It is the predominant method used in x-ray CT, and there is a need to correct acquired data used in projection imaging for the effects of patient motion.

The related application Ser. No. 07/615,778, now U.S. Pat. No. 5,121,128, referred to above, provides a method of modifying the back projecting process to accommodate motion of the patient occurring during acquisitions of the projections. In particular, the patient motion is modeled as a two dimensional magnification and offset of the volume elements (voxels) of the patient such as might occur with expansion of the chest during breathing.

The possibility of the above modification to the back projecting process was founded on an analyses of the image reconstruction process as a Fourier transform using the Fourier slice theorem. The results of this analyses were then applied to the more typically used back-projection process. The results suggested that the modification was appropriate provided the motion could be modeled as a simple, global magnification and offset of the voxels of the patient. Nevertheless, in general, the patient motion does not conform to a simple magnification and offset of the patient voxels but is a more complex function of time.

SUMMARY OF THE INVENTION

The present invention recognizes that the back-projecting process can be modified to correct for patient motion other than uniform magnification and offset providing the motion reduces locally to magnification and offset. The correction of the present invention occurs not on a global basis but point by point for each voxel of the patient, subject to the ability to construct a suitable modeling function of normal physiological motion.

Specifically, the method produces an image of a moving patient composed of a plurality of voxels, each voxel having a reference coordinate defined at a reference time during the patient motion, and a displaced coordinate, which at the reference time may equal the reference coordinate but at other times may not equal the reference coordinate. The patient is scanned to acquire a plurality of projections of a projection set at different times and throughout a range of different projection angles ($\theta$). Each projection measures a physical characteristic of the voxels at their displaced coordinates. Also acquired with each projection is a motion parameter indicating the movement of the patient as the projection is acquired.

The acquired projections are reconstructed by back projecting using a back projection formula which is modified by a predetermined warping function (G,H) that relates the displaced coordinates of the voxels to their reference coordinates as a function of the motion parameter. Artifacts, produced in the image by movement of the patient between projections are thus reduced.

In one embodiment, the back projecting employes the warping functions G and H to determine, along with the motion parameter, the displaced coordinates of each voxel (identified by its reference coordinate) at the time of the acquisition of the projection and backprojects the voxel at the reference coordinate but employing the displaced coordinate to identify the relevant information from the projection.

It is thus one object of the invention to provide an improved correction of motion in a scanned patient, such motion which may cause image artifacts, wherein the correction is responsive to a general warping function.

In a first embodiment, a method of calculating a Jacobian, employed prior to the modification of the back-projecting, is also provided, however, it has also been determined that in certain applications the Jacobian need not be employed, thus simplifying the calculational burden.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

CT Hardware

Figure 1:
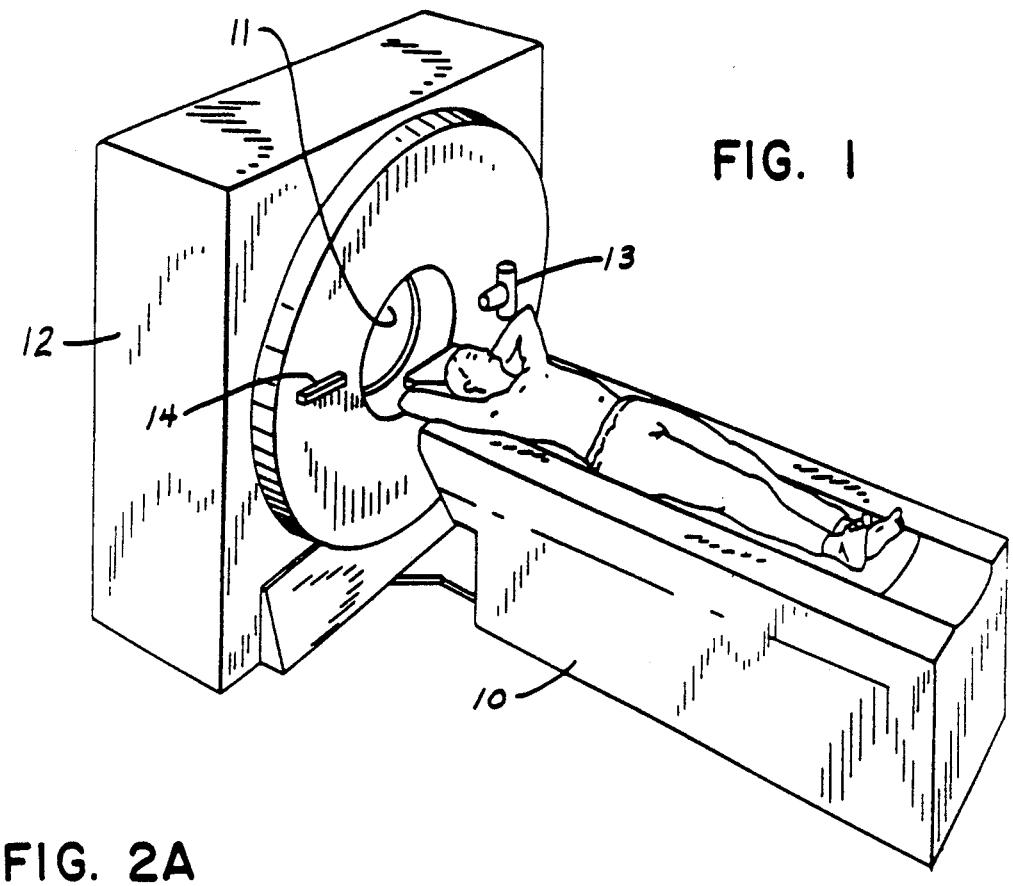
FIG. 1 is a perspective view of an x-ray CT scanner and patient.

While the present invention may be applied to many different imaging systems that employ back projection image reconstruction methods, the preferred embodiment is employed in an x-ray CT scanner such as that illustrated in FIG. 1.

As shown in FIG. 1, a CT scanner used to produce images of the human anatomy includes a patient table 10 which can be positioned within the aperture 11 of a gantry 12. A source of highly collimated x-rays 13 is mounted within the gantry 12 to one side of its aperture 11, and one or more detectors 14 are mounted to the other side of the aperture. The x-ray source 13 and detectors 14 are revolved about the aperture 11 during a scan of the patient to obtain x-ray attenuation measurements from many different angles.

Figure 2A:
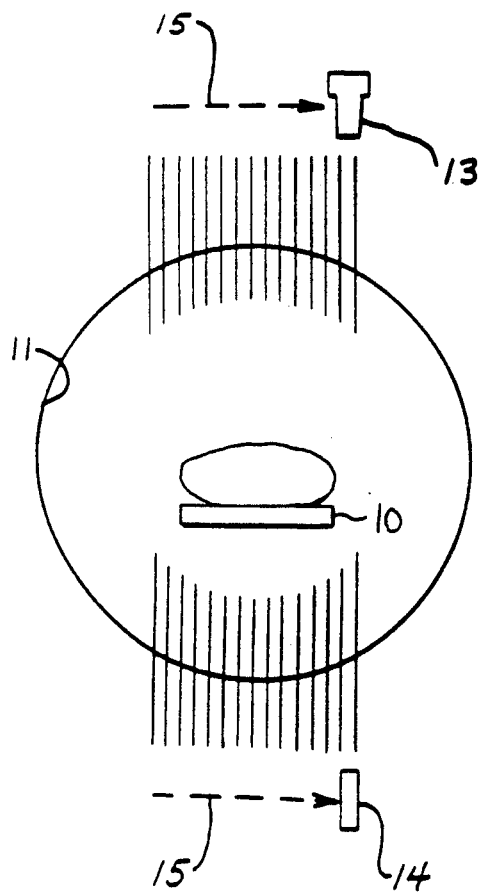
FIGS. 2A and 2B are schematic drawings of a parallel beam and a fan-beam scanning assembly on the scanner of FIG. 1.
Figure 2B:
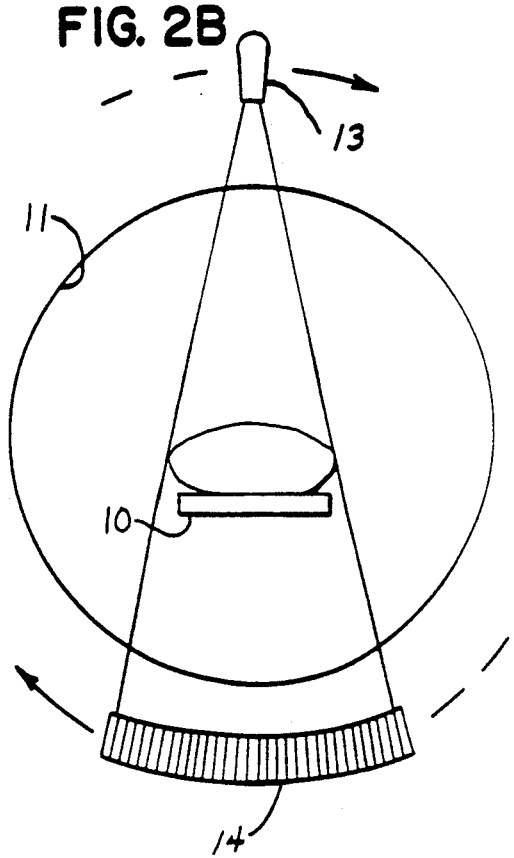

A complete scan of the patient is comprised of a set of x-ray attenuation measurements which are made at discrete angular orientations of the x-ray source 13 and detector 14. Each such set of measurements is referred to in the art as a "projection" and the results of each such set of measurements is a projection set. As shown in FIG. 2A, the set of measurements in each projection may be obtained by simultaneously translating the x-ray source 13 and detector 14 across the acquisition field of view, as indicated by arrows 15. As the devices 13 and 14 are translated, a series of x-ray attenuation measurements are made through the patient and the resulting set of data provides a transmission profile at one angular orientation ($\theta$). The angular orientation of the devices 13 and 14 is then changed (for example, 1°) and another projection is acquired. These are known in the art as parallel beam projections. An alternative structure for acquiring each transmission profile is shown in FIG. 2B. In this construction, the x-ray source 13 produces a fan-shaped beam which passes through the patient and impinges on an array of detectors 14. The detectors 14 can be curved as shown in FIG. 2B, or they can be aligned in a straight line (not shown in the drawings). Each detector 14 in this array produces a separate attenuation signal and the signals from all the detectors 14 are separately acquired to produce the transmission profile for the indicated angular orientation. As in the first structure, the x-ray source 13 and detector array 14 are then rotated to a different angular orientation and the next transmission profile is acquired.

As the data are acquired for each transmission profile, the signals are filtered, corrected and digitized for storage in a computer memory. These steps are referred to in the art collectively as "preprocessing" and they can be performed in real time as the data is being acquired. The acquired transmission profiles are then used to reconstruct an image which indicates the x-ray attenuation coefficient of each voxel in the reconstruction field of view. These attenuation coefficients are converted to integers called "CT numbers", which are used to control the brightness of a corresponding pixel on a CRT display. An image that reveals the anatomical structures in a slice taken through the patient is thus produced.

Figure 3:
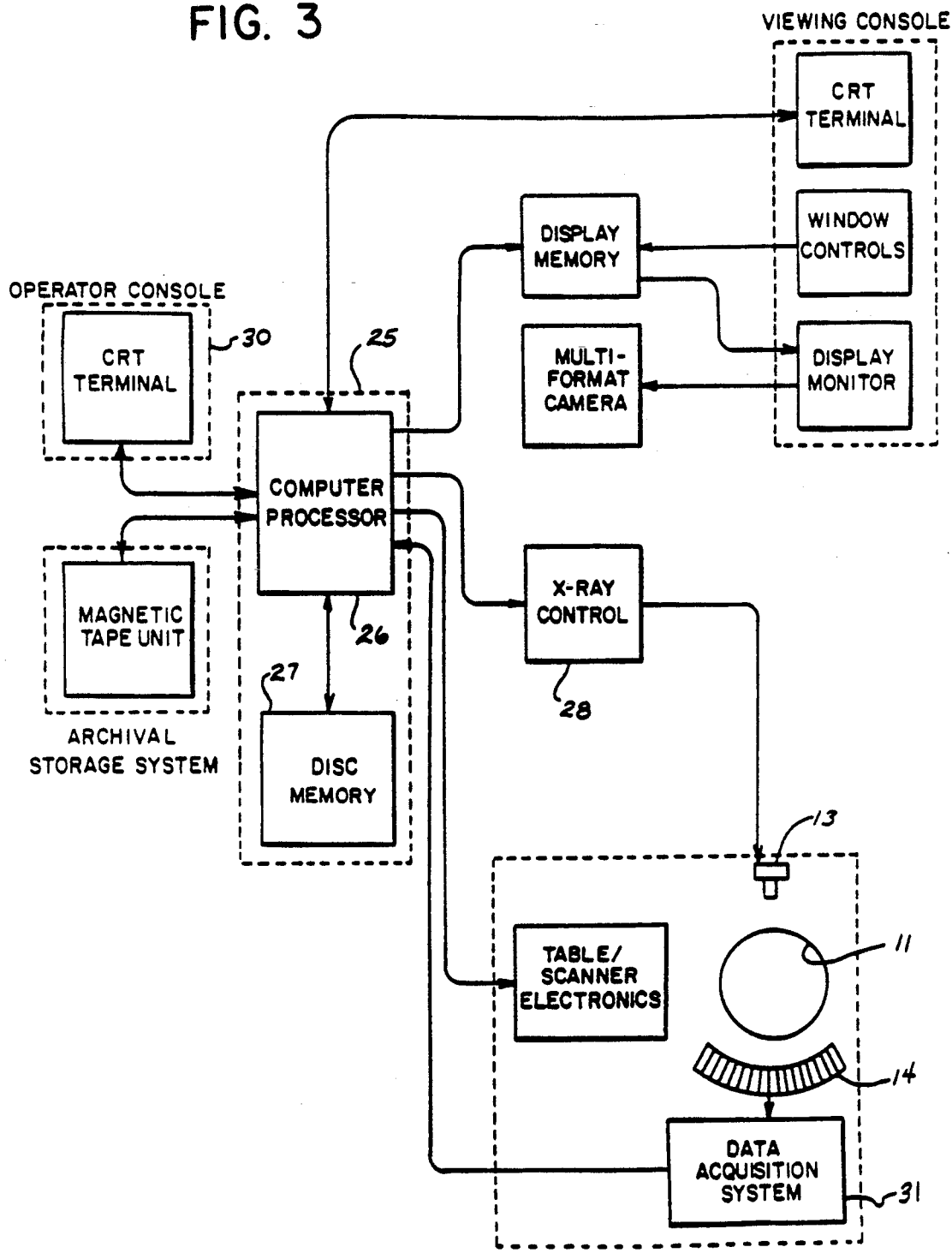
FIG. 3 is an electrical block diagram of the scanner of FIG. 1.

Referring particularly to FIG. 3, the operation of the CT system is controlled by a programmed data processing system 25 which includes a computer processor 26 and a disk memory 27. The disk memory 27 stores the programs the computer processor 26 uses in patient scanning and in image reconstruction and display. It also stores on a short-term basis the acquired data and the reconstructed image data. The computer processor includes a general purpose minicomputer with input and output ports suitable for connection to the other system elements as shown It also includes an array processor such as that disclosed in U.S. Pat. No. 4,494,141 which is incorporated herein by reference.

An output port on the computer processor 26 connects to an x-ray control circuit 28, which in turn controls the x-ray source 13. The high voltage on the x-ray source 13 is controlled and its cathode current is controlled to provide the correct dosage. The high voltage and cathode current are selected by an operator who enters the desired values through an operator console 30 and the computer processor 26 directs the production of the x-rays in accordance with its scan program.

The x-rays are dispersed in a fan-shape as described above and received by the array of detectors 14 mounted on the opposite side of the gantry aperture 11. Each individual cell, or detector element, examines a single ray originating from the x-ray source 13 and traversing a straight line path through a patient located in the aperture 11. The currents formed in each detector element are collected as an analog electrical signal and converted into a digital number by A/D converters in a data acquisition system 31. The digitized measurements from all the detectors is a complete projection. U.S. Pat. Nos. 4,112,303 and 4,115,695 disclose details of the gantry construction, U.S. Pat. No. 4,707,607 discloses the details of the detector array 14, and the data acquisition system is disclosed in U.S. Pat. No. 4,53,240. All of these patents are incorporated herein by reference. The digitized signals are input to the computer processor 26.

Figure 4:
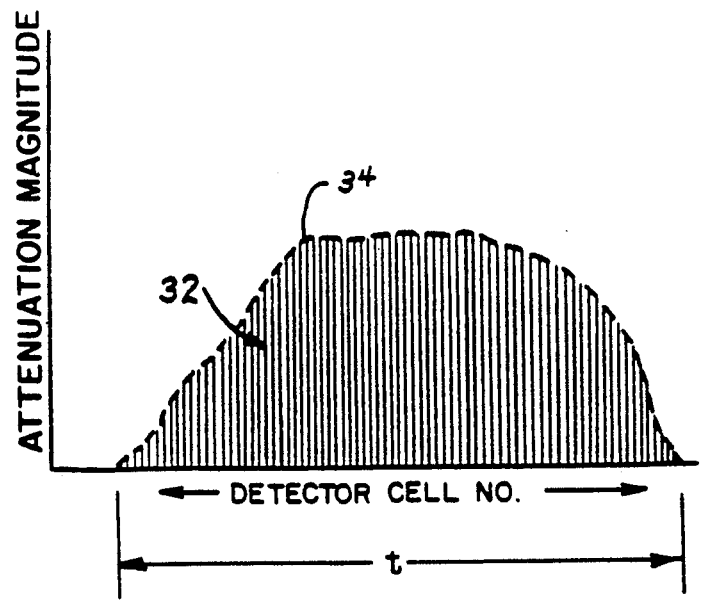
FIG. 4 is a graphic representation of one projection of data acquired by the scanner of FIG. 1.

The digitized attenuation measurements from the data acquisition system 31 are preprocessed in a well-known manner to compensate for "dark currents", for uneven detector cell sensitivities and gains, and for variations in x-ray beam intensity throughout the scan. This is followed by beam hardening corrections and conversion of the data to logarithmic form so that each measured value represents a line integral of the x-ray beam attenuation. This preprocessing is performed in real time as the scan is being conducted, and as shown in FIG. 4, each projection is comprised of a set of attenuation values 32 which define a transmission profile, or projection, indicated by dashed line 34.

In addition to the transmission profile data 34, two other pieces of information are input during the acquisition of each projection. The first is the angle ($\theta$) which indicates the angular orientation of the x-ray source 13 and detectors 14 with respect to the vertical reference axis. Typically, for example, the projections are acquired at 1° increments over a range of 180°.

Patient Motion

Figure 5:
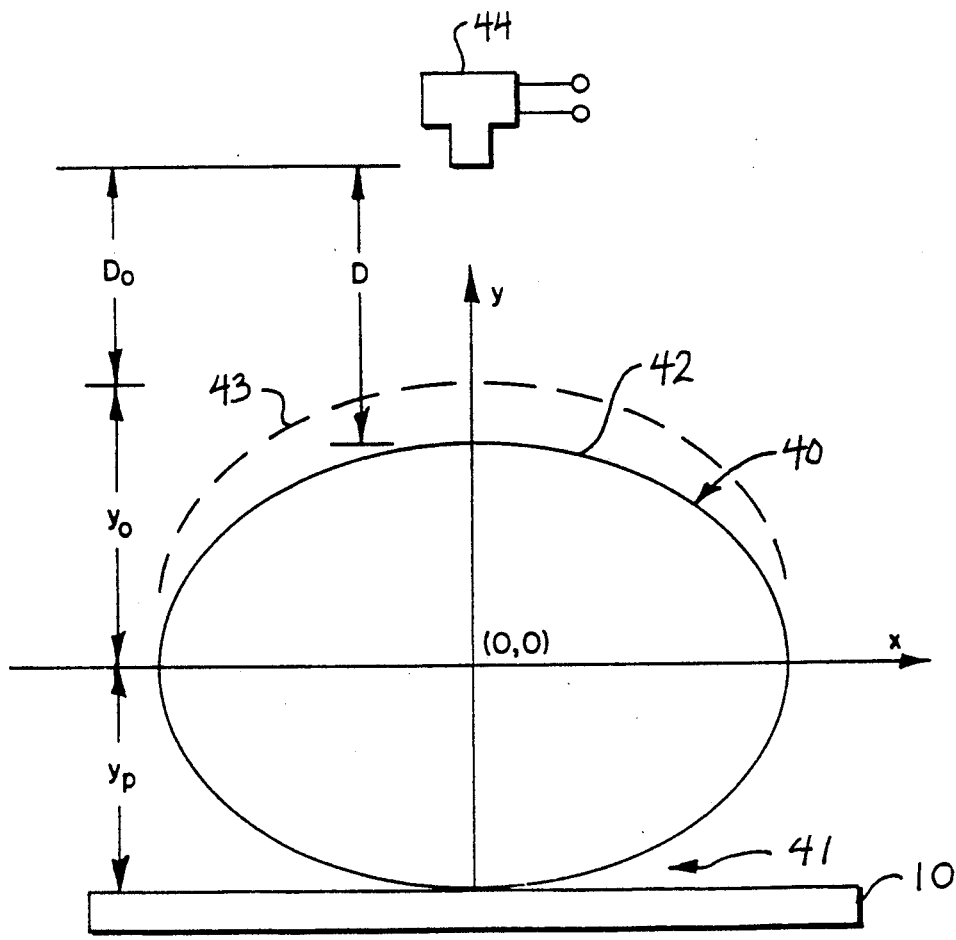
FIG. 5 is a schematic representation of a patient's chest cavity showing the orientation of a range finder that forms part of the scanner of FIG. 1.

The second piece of information acquired with each projection is a distance value (D) that is indicative of the position of the patient's chest cavity and which is a parameter employed in a geometric model of the chest cavity during respiration. Referring particularly to FIG. 5, this geometric model is illustrated by a schematic cross-section taken in a transverse plane through the patient's chest as indicated at 40. As the patient breathes the posterior chest wall 41 which rests on the supporting table 10 does not move any significant amount, whereas the anterior chest wall 42 moves vertically as indicated by the dashed line 43. As will be described below, the size and shape of the patient's chest cavity at any point in the respiratory cycle can be approximated by monitoring the vertical position of the anterior wall 42. Accordingly, an ultrasonic range finder 44 is mounted to the gantry 12 and is positioned to measure the vertical distance (D) to the patient's chest. This measured (D) is input to the computer processor 26 (FIG. 3) along with each projection of acquired data.

a. The Magnification-Shift Model of Patient Motion

Referring still to FIG. 5, as the patient breathes and the anterior chest wall 42 moves up and down, the contents of the chest cavity may be modeled as magnifying and shrinking along the vertical axis (y). This magnification does not occur about the center near $y=0$, but instead, at the posterior wall 41 located at $y=-y_p$. There is virtually no magnification along the horizontal (x), but to the extent that there is, it occurs about the center of the chest cavity at $x=0$ (if the patient is centered on the table 10). Using this model and the measured parameter D, a first embodiment of the present invention corrects the acquired projection data and employs the corrected projection data in the back projection reconstruction process such that the chest cavity appears stationary in a reference position during the entire scan. As a result, motion artifacts are significantly reduced or eliminated.

The corrections to the acquired data and the manner in which the corrected data is employed in the back projection process has been determined for a general case in which patient motion produces magnification along two axes (x and y) and the point about which magnification occurs is shifted, or offset, from the origin ($x=0$, $y=0$). The correction factors for this generalized case have been determined and will now be described.

Let f(x,y) be the cross-section of the patient which is to be reconstructed. A magnified and shifted version of this same cross-section during various stages of the patient motion cycle is given by:

$$f'(x,y) = f(\alpha_x + \beta_x x, \alpha_y + \beta_y y) \quad [1]$$

where $\beta_x$ and $\beta_y$ are magnification factors along the respective x and y axes and $\alpha_x$ and $\alpha_y$ are shift factors and where $\beta$ and $\alpha$ are functions of $\theta$. For parallel beam projection data the formula for projection of this magnified image at gantry rotational angle $\theta$ is given by:

$$P(\theta,t) = \int_{-\infty}^{\infty} \int_{-\infty}^{\infty} f'(x,y)\delta(t - x\cos\theta - y\sin\theta)dxdy \quad [2]$$

where $\delta(t)$ is the Dirac-delta function known to those skilled in this art. The Fourier transform of this projection can be found:

$$S'(\theta,\omega) = \int_{-\infty}^{\infty} f(\alpha_x + \beta_x x, \alpha_y + \beta_y y)e^{-j2\pi\omega(x\cos\theta + y\sin\theta)} dxdy \quad [3]$$

Now make the following changes of variables $$x' = \alpha_x + \beta_x x$$
$$y' = \alpha_y + \beta_y y \quad [4]$$

When [4] is used in [3], the following is obtained:

$$S'(\theta,\omega) = \int_{-\infty}^{\infty} \frac{f(x,y)}{|\beta_x\beta_y|} e^{-j2\pi\omega[\frac{x}{\beta_x}\cos\theta + \frac{y}{\beta_y}\sin\theta]} e^{j2\pi\omega[\frac{\alpha_x}{\beta_x}\cos\theta + \frac{\alpha_y}{\beta_y}\sin\theta]} dxdy \quad [5]$$

Let F(u,v) be the two-dimensional Fourier transform of f(x,y). Then it is seen that:

$$S'(\theta,\omega) = \frac{e^{j2\pi\omega[\frac{\alpha_x}{\beta_x}\cos\theta + \frac{\alpha_y}{\beta_y}\sin\theta]}}{\beta_x\beta_y} F\left[\frac{\omega\cos\theta}{\beta_x}, \frac{\omega\sin\theta}{\beta_y}\right] \quad [6]$$

This equation is a version of the Fourier Slice Theorem in the case of projections acquired from a magnified and shifted object function. It says that the Fourier transform of the projection at gantry position $\theta$ is a spoke of the two-dimensional Fourier transform of the object function at angle $$\theta' = \tan^{-1}\left[\frac{\beta_x}{\beta_y}\tan\theta\right] \quad [7]$$

after a phase term and a scaling factor have been removed.

Equations [6] and [7] could form the basis of a reconstruction algorithm which employs a two-dimensional Fourier transform of the data which results from the mapping of the one-dimensional Fourier transform of the projection data into the Fourier transform of the patient. This is not the preferred method of reconstruction. Instead, a filtered back projection method has been developed and will now be described in detail.

A filtered back projection reconstruction formula will now be derived for reconstructing f(x,y) using p'(θ,t). The inverse Fourier transform of F(u,v), is given by $$f(x,y) = \int_{-\infty}^{\infty} \int_{-\infty}^{\infty} F(u,v) \, e^{j2\pi(ux+vy)} \, du \, dv \qquad [8]$$

Consider the following change of variables $$u = \frac{\omega}{\beta_x} \cos\theta \qquad [9]$$

$$v = \frac{\omega}{\beta_y} \sin\theta$$

The components of the Jacobian in this change of variables are given by $$\frac{\partial u}{\partial \omega} = \frac{\cos\theta}{\beta_x} \qquad [10]$$

$$\frac{\partial u}{\partial \theta} = -\frac{\omega \sin\theta}{\beta_x} - \frac{\omega \beta'_x \cos\theta}{\beta_x^2}$$

$$\frac{\partial v}{\partial \omega} = \frac{\sin\theta}{\beta_y}$$

$$\frac{\partial v}{\partial \theta} = \frac{\omega \cos\theta}{\beta_y} - \frac{\omega \beta'_y \sin\theta}{\beta_y^2}$$

where $\beta'_x$ and $\beta'_y$ are the derivatives of $\beta_x$ and $\beta_y$ with respect to $\theta$. The Jacobian, $J(u,v,\omega, \theta)$, can be determined using [10] resulting in $$J(u,v,\omega, \theta) = |\omega \uparrow g(\theta)| \qquad [11]$$

where $$g(\theta) = \left| 1 + \frac{\sin 2\theta}{2} \left[ \frac{\beta'_x}{\beta_x} - \frac{\beta'_y}{\beta_y} \right] \right| / (\beta_x \beta_y) \qquad [12]$$

The value g(θ) is a weighting factor which is applied to the projection data at gantry position θ. In the parallel beam acquisition, this weighting factor is a constant value which is applied to each attenuation value 32 in the projection profile 34 at the position θ (FIG. 4). In some situations where the density of the object being imaged decreases as it is magnified, this weighting factor is modified to more closely approximate the geometric model of motion in equation [1]. More specifically, in such cases the weighting factor g(θ) should be multiplied by the value $\beta_y \beta_x$. The derivatives $\beta'_x$ and $\beta'_y$ can be calculated with numerical differences using the adjacent values of $\beta_x$ and $\beta_y$.

Using [9] and [11], [8] becomes $$f(x,y) = \int_0^\pi \int_{-\infty}^{+\infty} F\left[\frac{\omega \cos\theta}{\beta_x}, \frac{\omega \sin\theta}{\beta_y}\right] |\omega| g(\theta) \, e^{j2\pi\omega[\frac{x}{\beta_x}\cos\theta + \frac{1}{\beta_y}\sin\theta]} \, d\omega \, d\theta \qquad [13]$$

When [6] is used, [13] reduces to $$f(x,y) = \int_0^\pi q_\theta\left(\left[\frac{(x-\alpha_x)}{\beta_x}\right]\cos\theta + \left[\frac{(y-\alpha_y)}{\beta_y}\right]\sin\theta\right) d\theta \qquad [14]$$

where $$q_\theta(t) = \int_{-\infty}^{+\infty} S'(\theta,\omega) |\omega| g(\theta) e^{j2\pi\omega t} \, d\omega \qquad [15]$$

Equation [14] represents a filtered back projection formula for reconstruction of parallel projections that are acquired from the magnified and shifted object. The formula is valid for reconstructing any point in the x-y plane.

The image f(x,y) can be reconstructed, therefore, from a set of parallel beam projections acquired over a range of 180° gantry positions by modifying the conventional data acquisition and reconstruction method in the following manner. First, for each projection of the patient, not only is the attenuation profile data acquired, but also, the parameters $\alpha_x$, $\beta_x$, $\alpha_y$ and $\beta_y$ are measured. In the preferred embodiment, $\alpha_x$ is set to zero and $\beta_x$ is set to one since the patient is usually centered on the table 10 and there is very little magnification of the chest cavity along the x axis during respiration. Only $\beta_y$ and $\alpha_y$ are required, therefore, to significantly reduce motion artifacts in the chest cavity and these are measured indirectly. As shown in FIG. 5, the distance between y=0 and the point about which magnification occurs is fixed at $-y_p$. Also, the distance between the range finder 44 and this same point is fixed. As a result, the values for $\beta_y$ and $\alpha_y$ can be calculated from these fixed values and the measurement (D) produced by the range finder 44 as follows:

$$\beta_y = 1/(1+(D-D_0)/(y_0+y_p)) \qquad [16]$$

$$\alpha_y = -y_p(1-\beta_y) \qquad [17]$$

where $y_0$ is a reference position for the anterior chest wall which is selectable by the operator and which determines the shape and size of the reconstructed image, and $D_0$ is the range finder measurement at this reference position. Consequently, the distance measurement (D) is acquired along with each projection profile and this measured parameter is sufficient to indicate the shape and size of the patient's chest cavity at the moment the projection was acquired.

b. A Generalized Warping Function Model Of Patient Motion

In a second embodiment, it has been recognized that this technique of correction may be expanded to two-dimensional temporally and spatially varying motion as may be described by a general function dependent on space and time f'(x,y)=f(x',y') and x' and y' are determined from generalized warp functions:

$$x' = G(x,y,\theta) \qquad [18]$$

$$y' = H(x,y,\theta) \qquad [19]$$

where (x', y') are the Cartesian coordinates of some voxel displaced from a reference position (x,y) and θ is gantry position and proportional to time and G and H are warping functions. Employing a similar analysis as that provided above, projections acquired from the body undergoing the generalized motion of equations [18] and [19] is given by the following Radon transform:

$$P'(\theta,t) = \int_{-\infty}^{\infty} \int_{-\infty}^{\infty} f(x',y')\delta(t - x'\cos\theta - y'\sin\theta)dx'dy' \quad [20]$$

where P'($\theta$,t) is the projection value at t and $\theta$ and $\delta$ is the Dirac delta function. After the projections P'($\theta$,t) are filtered, the filtered projections q($\theta$, t) are backprojected as follows.

$$f(x,y) \approx \int_0^\pi q_\theta([G^{-1}(x',y',\theta)]\cos\theta + [H^{-1}(x',y',\theta)]\sin\theta) \quad [21]$$

where $G^{-1}$ and $H^{-1}$ are the solutions of equations [18] and [19] for x and y respectively.

Equation [21] follows from equation [14] and the assumption that equation [4] is satisfied by the warping functions G and H over a small area. In other words, the warping functions must be capable of approximation locally as magnification and offset, e.g. the warping functions must be non-rotational. The validity of this assumption has been established through computer simulation.

As can be seen from equation [21], the voxels (x,y) are reconstructed according to their reference coordinates, however, the data of the filtered projections employed in the backprojecting is determined from the displaced coordinates (x',y') of those voxels as determined from the warping functions G and H, not from the reference coordinates (x,y).

Because warping functions G and H are not restrained to be uniform magnification and offset, in general no $\beta$ values exist to compute the Jacobian or the value of g($\theta$) as computed in equation [11] above. Nevertheless, a Jacobian can be computed by considering an arbitrarily small volume of the patient in which the generalized warp functions G and H devolve to a simple magnification and shifting as described above.

When we consider more complex warping functions such as those in [18] and [19], the derivatives with respect to x in the $\alpha$ and $\beta$ terms simply become partial derivatives. To compute g($\theta$), we need $\beta$x and $\beta$y which are given by:

$$\beta_x \approx \frac{\partial G}{\partial x} \quad [22]$$

$$\beta_y \approx \frac{\partial H}{\partial y} \quad [23]$$

Using these $\beta$ values, it is now possible to compute the Jacobian g($\theta$) and recover f(x,y) from projections of f(x',y'). It has been determined that the Jacobian values are approximately unity for actual patients where the density of the patient decreases with increase in patient volume and hence the Jacobians may be ignored in many practical situations.

The ability to employ a generalized warping function allows different models of particular patient motion to be employed, models that may more accurately reflect the actual motion. For example, one such model, differing from that described above with respect to equations [1], is radial expansion about a point (x$_0$, y$_0$) as given by the following equations:

$$G(x,y,\theta) = x' = \begin{cases} d\left[\dfrac{m(\theta)\cos\alpha}{m(\theta) - (m(\theta) - 1)\sin\alpha}\right] & \pi \geq \alpha > 0 \\ x & \text{elsewhere} \end{cases} \quad [24]$$

$$H(x,y,\theta) = y' = \begin{cases} d\left[\dfrac{m(\theta)\sin\alpha}{m(\theta) - (m(\theta) - 1)\sin\alpha}\right] & \pi \geq \alpha > 0 \\ y & \text{elsewhere} \end{cases} \quad [25]$$

where m($\theta$) is the expansion factor and linearly related to D the motion parameter and d is the distance between the center of expansion and the point that is moving and $$\sqrt{(x - x_0)^2 + (y - y_0)^2} \text{ and } \alpha = \arctan\frac{y - y_0}{x - x_0}.$$

Equations [24] and [25] are an empirical description of actual respiration which has been shown by computer simulation to satisfy the assumptions of equation [21].

CT Software

The preferred embodiment of the invention will now be described with reference to the flow chart of FIG. 6. While most of the steps are carried out in dedicated hardware so that the processing can be carried out in "real time", the process itself is controlled by a program executed by the computer 26 which performs the scan.

This control program is entered at 75 and the CT system is initialized at process block 76 to acquire the data for the first projection. This includes receiving input data from the operator such as the reference chest position y$_o$ and reference range finder distance D$_0$, and orientation of the gantry to the desired starting position of $\theta = -90°$. A loop is then entered in which the profile data for the first projection is acquired and preprocessed as indicated at block 77. The distance measurement (D) from the range finder 44 (FIG. 5) is acquired at process block 78 and motion factors are calculated at process block 79. The motion factors may be the values for $\beta_y$ and $\alpha_y$ calculated using the equations [16] and [17] or may be related to the more complex warping functions of equations [18] and [19]. In the latter case, distance measure D and the reference value D$_0$ are used to deduce the parameters of the warping functions and to synchronize the warping function with the actual motion of the patient.

The acquired projection data is filtered in the usual fashion at process block 80 and then it is weighted at process block 81 by multiplying each value in the profile data set by the weighting factor g($\theta$) calculated in accordance with equation [12] or with respect to warping function G and H, as indicated generally at equations [18] and [19].

The corrected projection data is employed in reconstructing an image using the back projection technique as indicated at process block 82, however, as indicated by equation [14] and [21], this process is modified to account for motion.

Figure 7:
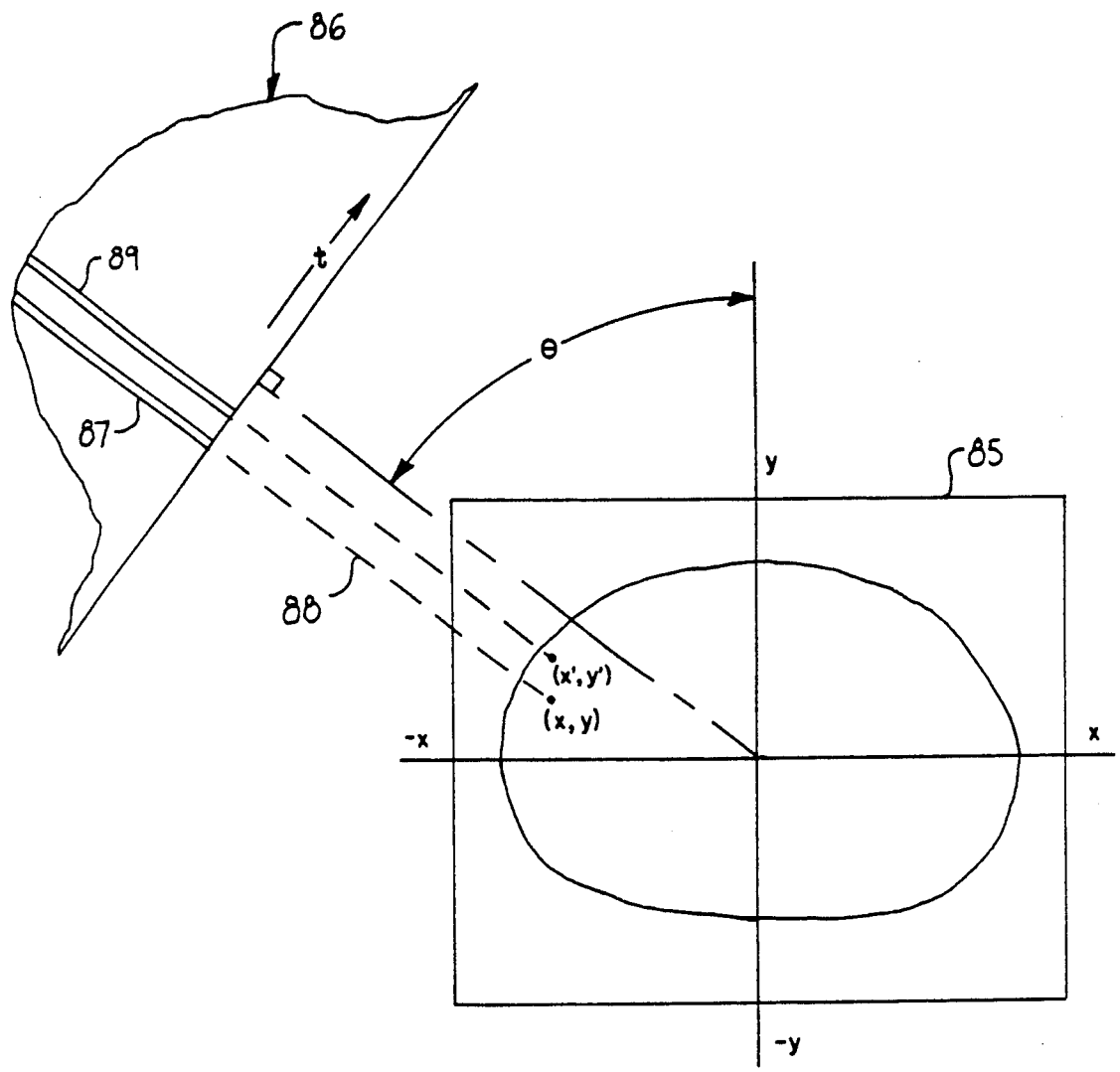
FIG. 7 is a schematic representation of one of the steps employed by the program of FIG. 6.

Referring particularly to FIG. 7, a 512 by 512 pixel image 85 is created by determining which of the values in the corrected and filtered projection data set 86 contribute to the brightness value of the pixel located at reference coordinates (x,y). In a parallel beam acquisition, the conventional back projection formula for determining which value (t) to use is as follows:

$$t = x\cos\theta + y\sin\theta \quad [26]$$

where (x,y) is the location of the pixel, $\theta$ is the projection angle for the projection, and t is the location in the projection data set from which an attenuation value 87 is read. This conventional back projection is shown in FIG. 7 by the dashed line 88. Typically, t is located between two samples in the acquired data set and interpolation is used to determine a more accurate value to be added to the CT number for pixel (x,y). For each projection, all of the pixels in the image 85 are processed in this fashion to determine the contribution to their accumulated CT numbers.

To practice the present invention this back projection technique is changed to select a different value (t') from the corrected projection data set 86. This selection is made as follows:

$$t' = x'\cos\theta + y'\sin\theta \quad [27]$$

where in the first embodiment:

$$x' = (x - \alpha_x)/\beta_x \quad [28]$$

$$y' = (y - \alpha_y)/\beta_y \quad [29]$$

and in the second generalized embodiment:

$$x' = G^{-1}(x,y,\theta) \quad [30]$$

$$y' = H^{-1}(x,y,\theta) \quad [31]$$

Note that x' and y' are used differently than previously defined.

In both cases the back projection process is modified by a displacement factor. This change is illustrated in FIG. 7 where (x,y) is the pixel in the reference image being reconstructed, (x',y') is the location of the same point in the patient, at the time the projection data was actually acquired, and the attenuation value 89 is the value selected by equation [19]. In other words, the geometric model and the motion parameter D indicate that the attenuation value to be used at the pixel (x,y) from the projection data 86 is the value 89 at t' rather than the attenuation value 87. After the contribution to each pixel in the image has been computed, the system loops at decision block 90 to advance the gantry and acquire and process that data for the next projection. When 180° of data have been acquired and processed in this manner, the scan is complete and the image data 85 is displayed at process block 91. The CT numbers in the image data array 85 are scaled and processed in the normal fashion to produce an image of the desired brightness level and range.

The teaching of the present invention is also applicable to fan-beam CT scanners which employ the back projection technique of image reconstruction. As in the first and second embodiments described above, the acquired projection data is corrected by a weighting factor including a Jacobian, and the back projection process is modified by a displacement factor. The calculation of the weighting factors and displacement factors depend on the model of motion employed and the geometry of the scanner. Two examples, using the magnification and shifting model of equation [12] and a fan beam of x-rays received by a flat and curved detector are now provided.

Fan Beam with Flat Detector

Figure 6:
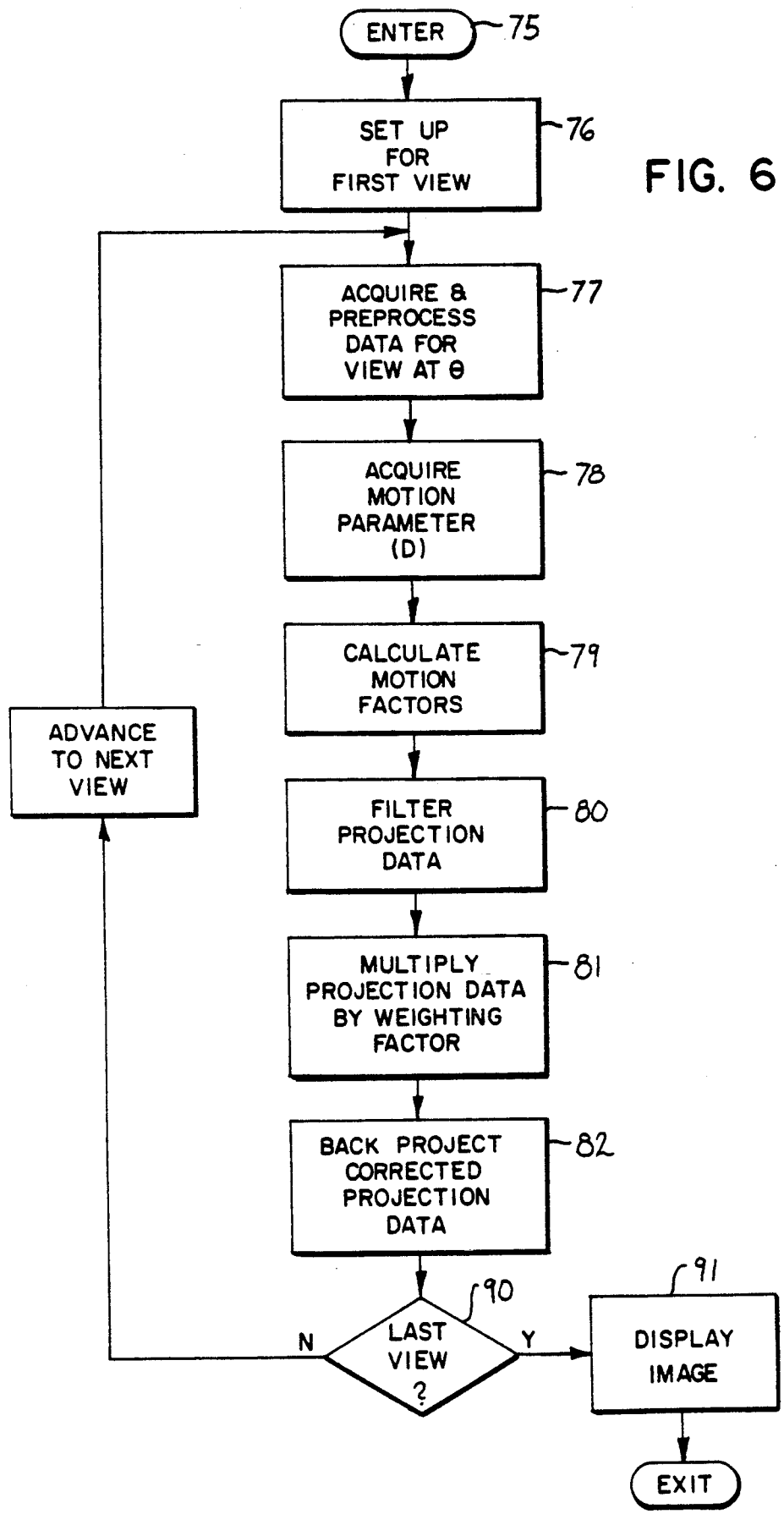
FIG. 6 is a flow chart of the program executed by the CT scanner of FIG. 1 to carry out the preferred embodiment of the invention.

For a flat detector fan-beam reconstruction the weighting factor used in process block 81 in FIG. 6 is as follows:

$$G(S,\alpha) = 1 + \frac{\sin 2(\alpha + \tan^{-1} S/R)}{2}\left[\frac{\beta'_x}{\beta_x} - \frac{\beta'_y}{\beta_y}\right]\frac{RZ}{2\beta_x\beta_y} \quad [32]$$

where $\alpha$ is the rotational position of the gantry, s is the position of the x-ray detector which is being weighted with respect to the center of the detector array, R is the distance between the x-ray source and the center of the detector array, and $$Z = \sqrt{R^2 + S^2} \quad [33]$$

In contrast to the parallel beam acquisition, this weighting factor not only varies as a function of gantry position $\alpha$, but also as a function of the location of the detector in the flat array. During the back projection process of block 82 a different formula than equation [27] is used for selecting the proper attenuation value for each pixel (x,y). Many back projection formulas are known in the art such as that described in U.S. Pat. No. 4,812,983 entitled "Method and Means of Correcting For a Shift in the Center of Rotation of a Rotating Fan-Beam CT System" which is incorporated herein by reference. Regardless of the formula used, the displacement factor of the present invention is applied by substituting the values of x' and y' given above in equations [28] and [29] for the values of x and y respectively in the particular back projection formula used.

Fan Beam with Curved Detector

For a curved detector fan-beam reconstruction the weighting factor used in process block 81 in FIG. 6 is as follows:

$$G(\alpha,\gamma) = 1 + \frac{\sin 2(\alpha + \gamma)}{2}\left[\frac{\beta'_x}{\beta_x} - \frac{\beta'_y}{\beta_y}\right]\frac{R\cos\gamma}{2\beta_x\beta_y} \quad [34]$$

where $\alpha$ is the rotational position of the gantry, R is the distance between the x-ray source and the central axis of rotation of the gantry, and $\gamma$ is the angle as measured at the x-ray source between the central array detector and the detector whose signal is being weighted. During the back projection process of block 82, the values of x' and y' given above in equations [28] and [29] are substituted for the values of x and y respectively in the formula used for back projection.

While the theory indicates that the weighting factors must be applied to correct the projection data before it is used to reconstruct an image according to the present invention, experimental results have shown that this is not always required. In many cases, a substantial reduction in motion artifacts can be achieved without applying the weighting factor and only applying the displacement factor to the back projection process.

It should be apparent to those skilled in the art that the present invention is applicable to many different back projection reconstruction techniques. Regardless of the back projection technique used, a weighting factor can be calculated for each acquired attenuation value in the data set and the back projection process can be modified by substituting the displacement factors of equations [18], [19], [28] and [29] into the back projection formula. This is true regardless of the modality used to acquire the projection data. Thus, for example, projection data acquired with PET, MRI or SPECT scanners can be corrected for patient motion according to the teachings of the present invention.

It is well-known that in x-ray CT fan-beam reconstruction certain factors can be applied to projection data to diminish the effects of patient motion. While the mathematics suggests that the present invention will not work with such prior methods, experimental results have demonstrated that some improvement is in fact obtained when the present invention is used in combination with such techniques.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. A method for producing an image of a moving patient composed of a plurality of voxels, each voxel having reference coordinate defined at a reference time while the patient is in motion, and a displaced coordinate which at the reference time may equal the reference coordinate, but at other times may not equal the reference coordinate, the steps comprising:

performing a scan in which a plurality of projections of a projection data set are acquired at different times and throughout a range of different projection angles ($\theta$), each projection measuring physical characteristic of the voxels at their displaced coordinates;

acquiring a motion parameter with each projection of the projection set, each acquired motion parameter being indicative of the movement of the patient as the projection set is acquired; and back projecting the set of projections to produce the image of the patient using a back projection formula which is modified to account for the displacement of the voxels from their reference coordinates at the time of the projection is acquired, the modification being according to a predetermined warping function that relates the displaced coordinates of the voxels to their reference coordinates as a function of the motion parameter;

whereby artifacts produced in the image by movement of the patient from projection-to-projection during the scan are reduced.

2. The method as recited in claim 1 in which the motion parameter acquired with each set of projection data indicates the position of the anterior chest wall of the patient.

3. The method as recited in claim 1 wherein the step of backprojecting includes for each voxel at a reference coordinate and for each projection:

a) employing the warping function to determine from the motion parameter the displaced coordinates of that voxel at the time of the acquisition of the projection; and b) backprojecting the voxel at the reference coordinate but employing the displaced coordinate to identify data from the projection used for the backprojection.

4. The method as recited in claim 3 in which the motion parameter acquired with each projection indicates the position of the anterior chest wall of the patient and the warping function provides a displacement coordinate for each voxel based on the position of the anterior chest wall, the reference coordinate of the voxel, and a motion reference value which indicates the position of the anterior chest wall of the patient at a predetermined point in the patient's respiratory cycle.

5. The method as recited in claim 1 in which the projection data is x-ray attenuation values.

6. The method as recited in claim 5 in which the motion of the patient is due to respiration and the warping function is calculated based on a geometric model of the motion of the patient's chest cavity during respiration and the acquired motion parameter which indicates a position of the patient as the projection set is acquired.

7. The method as recited in claim 1 in which the set of projection data is acquired with parallel x-ray beams.

8. The method as recited in claim 1 in which the set of projection data is acquired with a curved array of x-ray detectors that receive a fan-beam of x-rays.

9. The method as recited in claim 1 in which the set of projection data is acquired with a flat array of x-ray detectors that receive a fan-beam of x-rays.

* * * * *